United States Patent [19]

McCutchan et al.

[11] Patent Number: 4,693,994

[45] Date of Patent: Sep. 15, 1987

[54] PROTECTIVE SYNTHETIC PEPTIDE AGAINST MALARIA AND ENCODING GENE

[75] Inventors: Thomas F. McCutchan, Silver Spring; Richard Wistar, Jr., Bethesda, both of Md.

[73] Assignee: The Government of the United States of America as represented by the Secretary of the Department of Health and Human Services, Washington, D.C.

[21] Appl. No.: 799,464

[22] Filed: Nov. 19, 1985

[51] Int. Cl.[4] .................... A61K 37/02; C07K 7/06
[52] U.S. Cl. .................................. 514/15; 530/328
[58] Field of Search ............... 530/350, 322, 328; 514/15

[56] References Cited

U.S. PATENT DOCUMENTS 4,466,917  8/1984  Nussenzweig et al. ............ 530/350
4,574,058  3/1986  Baschang et al. .................. 530/322

FOREIGN PATENT DOCUMENTS

WO84/02922  8/1984  PCT Int'l Appl. .

OTHER PUBLICATIONS

J. Exp. Med. 160, (1984), 935–940.
Science 230, (1985), 1381–1383.
Science 228, (1985), 996–9.
Dame et al., Science 225:593–599 (1984).
Arnot et al., Science 230:815–818 (1985).

Primary Examiner—Delbert R. Phillips
Attorney, Agent, or Firm—Holman & Stern

[57] ABSTRACT

The present invention discloses a synthetic peptide capable of inducing antibodies protective against human malarial infection caused by *Plasmodium vivax* sporozoites and the cloning of a gene encoding said peptide. The amino acid and nucleotide sequences of the peptide and the gene, respectively, have been determined and described.

4 Claims, 2 Drawing Figures

```
                                                  *                                                *
P. vivax     AAT GGA GTA AAC TTC AAT AAT GTA GAC GCG AGT TCA CTT GGC GCA CAC GTA GGA CAA
             Asn Gly Val Asn Phe Asn Asn Val Asp Ala Ser Leu Gly Ala Ala His Val Gly Gln P. knowlesi  Asn Gly Val Ser Phe Asn Asn Val Asp Thr Ser Ser Leu Gly Ala Gln Val Arg Gln

*                                    *                                    *
P. vivax     AGT GCT AGC CGA GGC AGA GGA CTT GGT GAG AAC CCA GAT GAC GAG GAA GAT GCT AAA
             Ser Ala Ser Arg Gly Arg Gly Leu Gly Glu Asn Pro Asp Asp Glu Glu Asp Ala Lys P. knowlesi  Ser Ala Ser Arg Gly Arg Gly Leu Gly Lys Pro Lys Pro Gly Gly Ala Asp Lys Glu Lys

*                    !<------Region I--
P. vivax     AAA AAA AAG GAT GGA AAG --- AAA --- GCA GAA CCA AAA AAT CCA CGT GAA AAT AAG CTG
             Lys Lys Lys Asp Gly Lys --- Lys --- Ala Glu Pro Lys Asn Pro Arg Glu Asn Lys Leu P. knowlesi  Lys Lys Lys Gly Gly Lys Glu Glu Pro Lys Pro Asn Glu Asn Lys Leu ------>!                                                            *
P. vivax     AAA CAA CCA GGA GAC AGA GCA GAT GGA CAG CCA GGA CAG GAC AGA GCA GAT GGA CAG CCA
             Lys Gln Pro Gly Asp Arg Ala Asp Gly Gln Pro Gly Gln Asp Arg Ala Asp Gly Gln Pro
                    !-------------------------!                            !-------------------------!
                                            *
P. knowlesi  Lys Gln Pro Asn Glu Gly Gln Pro Gln Ala Gln Gly Asp Ala Asn Ala Gly Gln Pro
                    !-----------------------!

*
P. vivax     GCA GGA GAC AGA GCA GAT GGA CAG CCA GGT GAT AGA GCA GAT GGA CAA CCA GGA
             Ala Gly Asp Arg Ala Asp Gly Gln Pro Gly Asp Arg Ala Asp Gly Gln Pro Ala Gly
             --!                                              !--

P. knowlesi  Gln Ala Gln Gly Asp Gly Ala Asn Ala Gly Gln Pro Gln Ala Gly Asp Gly Ala Asn
                                                  !--                            !--
```

Figure 1

```
P. vivax (SalI)        ... Asn Pro Arg Glu Asn Lys Leu Lys Gln Pro  Gly Asp Arg Ala Asp Gly Gln Pro Ala ...
P. knowlesi (Nuri)     ... Lys Pro Asn Glu Asn Lys Leu Lys Gln Pro  Glu Gln Pro Ala Ala Gly Ala Gly Gly ...
P. knowlesi (H)        ... Lys Pro Asn Glu Asn Lys Leu Lys Gln Pro  Asn Glu Gly Gln Pro Gln Ala Gln Gly Asp Gly Ala Asn Ala ...
P. falciparum          ... Lys Pro Lys His Lys Lys Leu Lys Gln Pro  Gly Asp Gly Asn Pro Asp Pro Asn Ala Asn Pro
```

Figure 2

PROTECTIVE SYNTHETIC PEPTIDE AGAINST MALARIA AND ENCODING GENE

BACKGROUND OF THE INVENTION

1. Technical Field

The present invention is related to a synthetic peptide capable of inducing antibodies protective against human malarial infection caused by *Plasmodium vivax* sporozoites and the cloning of a gene encoding said peptide.

2. State of the Art

Of the four human malarias, *Plasmodium vivax* and *P. falciparum* are the most common and are a major cause of the malarial disease in the Tropics. Controlling these two infections would indeed improve health conditions in those regions of the globe where malarial infection still remains a major disease causing factor.

One approach has been the development of vaccines against the different stages in the parasite's life cycle. Sporozoites, the stage inoculated by mosquitoes to initiate the human infection, are covered with a particular protein known as the circumsporozoite (CS) protein. Antibodies to the CS protein have been shown to block infection in vivo (*Potocnjak, et al., J. Exp. Med.* 151:1504, 1980). Recently, the gene for the CS protein of *P. falciparum* was cloned, using anti-CS protein antibody screening of a mung bean nuclease digested genomic DNA library (*Dame et al., Science* 225:593, 1984) or of a cDNA library from sporozoite mRNA (*Enea et al., Science* 225:628, 1984). Recombinant (*Young et al., Science* 228:958, 1985) and synthetic peptide antigens (*Ballou et al., Science* 228:996, 1985; *Zavala et al. Science* 228:1437, 1985) of the repeat region in the middle of the CS protein of *P. falciparum* induce antibodies which block sporozoite invasion of liver cells in vitro.

The nature and function of the immunodominant epitope of the surface protein on sporozoites of the human malarial parasite *Plasmodium vivax* (*P. vivax*) has not heretofore been known.

SUMMARY OF THE INVENTION

It is, therefore, an object of the present invention to characterize the nature of the immunodominant epitope of the surface protein of *P. vivax* sporozoite and to identify, isolate and clone the gene encoding said epitope.

It is a further object of the present invention to provide a synthetic peptide capable of inducing antibodies protective against malarial infection caused by *P. vivax* sporozoites and a cloned gene capable of directing the synthesis of said peptide in a suitable genomic medium.

Other objects and advantages will become apparent as the detailed description of the present invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows the nucleotide sequence of the immunodominant region of the CS protein of *P. vivax*. The deduced amino acid sequence of the CS protein is given beneath the nucleotide sequence. The amino acid sequence of the comparable region of the *P. knowlesi* (H) CS protein gene from amino acid 35 to amino acid 134 is also given for comparison. Dashes (---) interrupting the *P. vivax* sequences represent gaps in comparison to the *P. knowlesi* sequence. The bounds of Region I are indicated. The repeated sequences are underlined; and FIG. 2 shows the region of sequence homology among the CS proteins of *P. vivax*, *P. falciparum* and *P. knowlesi* (H and Nuri strains). Amino acid sequence homologies are boxed. Repeated sequences are underlined.

DETAILED DESCRIPTION OF INVENTION

The above objects and advantages of the present invention are achieved by a synthetic peptide having, at least in part, the aminoacid sequence Gly-Asp-Arg-Ala-Asp-Gly-Gln-Pro-Ala and a cloned gene capable of directing the synthesis of said peptide in a suitable genomic medium, said gene having, at least in part, the nucleotide sequence GGA-GAC-AGA-GCA-GAT-GGA-CAG-CCA-GCA.

It is noted that those technical terms or phrases used herein which have not been specifically defined have the same meaning as generally understood by one of ordinary skill in the art to which this invention belongs.

The term "synthetic" as used herein is intended to indicate that the circumsporozoite (CS) protein from *P. vivax* occurring in its natural state is specifically excluded from the peptides of this invention. The present invention rests in part on the discovery of the structure of the epitopes of the CS protein and on the ability of antibodies against these epitopes to produce immunity against malaria. Once the structure of the epitope becomes known, it becomes possible to design synthetic peptides useful as vaccines. Synthetic here does not, however, exclude production by biological methods in which human have intervened, for example by genetic engineering in the production of cloned genes and the like.

An important characteristic of the peptides of the present invention is that they are immunologically active and are capable of inducing a human response which is cross reactive against infection by a malaria parasite either alone or when attached to a carrier molecule. Accordingly, it is necessary that at least part of the enumerated sequences be present on an immunogenically avaiable surface of a peptide containing one or more of these sequences. Several methods are available for designing a peptide having these characteristics and one of ordinary skill can easily prepare the same from techniques well known in the art.

First, it is possible to chemically or biochemically synthesize a peptide in which the peptides consist essentially of the enumerated sequences. Such peptides would contain at least 10% of their amino acids in the enumerated sequences, preferably at least 40%, more preferably at least 60%, and most preferably at least 80%. Most preferred are peptides which consist entirely of the enumerated sequences (along with peptides which can be considered as consisting of the enumerated repeat sequence in which 1-3 terminal amino acids of the peptide are missing from either or both ends of the peptide).

It is also possible to design peptides in which the enumerated sequences of amino acids are found on the surface of the final peptide. This can be done, for example, by attaching one or more of the enumerated sequences to a surface of a previously prepared peptide by means of a peptide bond.

However, even in the event that one or more of the enumerated sequences is contained within the interior of the amino acid sequence of a larger synthetic peptide or protein, those skilled in the art of immunology can readily determine if the peptide falls within the scope of the present invention. Only those peptides which are reactive with antibodies raised against CS proteins are considered to be within the scope of the present invention. Accordingly, one skilled in the art may readily synthesize a peptide containing one of the sequences of the present invention and then determine by routine testing whether or not the finished product is within the scope of the present invention by reacting the protein with an antibody (preferably a monoclonal antibody) raised against a CS protein, preferably a CS protein of *P. vivax*, or against a peptide consisting essentially or entirely of one of the sequences specifically set forth in this application. If a positive immunological reaction takes place, the protein falls within the scope of the present invention.

There is no upper limit on the size of molecules of the invention, other than those limits set by the ability to synthesize large peptide molecules. Molecules of the invention can be either soluble or insoluble in aqueous solutions. In fact, one preferred embodiment of the invention involves the synthesis of high molecular weight, insoluble peptides which can be ground and injected as an aqueous suspension in order to induce immunological protection. Nevertheless, smaller molecules are also suitable for carrying out the invention. Molecules containing 100, 200, 400, or even 1,000 repeat units are suitable for the practice of the present invention. However, there appears to be no necessity of synthesizing peptides containing more than fifty repeat since peptides containing up to fifty repeat units will be sufficient to induce the desired immunological effect and are easier to synthesize. Molecules with 20 to 50 repeat units are particularly preferred. Peptides which contain up to 50 repeat units in which the repeat units form at least 40%, more preferably 80%, of the entire peptide are preferred.

The preferred method of synthesizing peptides of the invention containing repeat units is formation of one or more nonamer of the desired structure followed by polymerization of the nonamer to produce the final product. Very large peptides can be produced in this manner. Such chemical synthesis is also preferred when a long repeat sequence is present as part of a larger molecule. The repeating sequence and the shorter variable sequences can be synthesized independently and then joined to produce the desired final products. Such techniques are well within the skill of those knowledgeable in peptide synthesis. For example, U.S. Pat. No. 4,132,746 describes the synthesis of peptide tetramers and the polymerization of the tetramers to form larger molecules. The method described therein can easily be adapted to the present invention by selecting the amino acids described herein instead of the amino acids listed in the patent.

Of course, with the advent of modern peptide synthesizers, many of which are available commercially, it has become increasingly easier to synthesize either complete large peptide molecules or synthesize large fragments which can then be joined in turn.

Before a description of the genetic (biological) methods of synthesizing peptides of the invention is given, it will be useful to consider a preferred embodiment of the invention in which the ability of peptides of the invention to induce immunological response is enhanced by bonding one or more of the peptides of the invention to an immunogenic carrier. The resulting product, having enhanced immunogenicity, is referred to herein as an antimalarial immunogenic stimulant.

The use of immunogenic carriers to enhance the immunogenicity of small molecules is well known. Carriers are basically divided into two classes, soluble molecules and particles. Typical examples of soluble molecules are proteins and polysaccharides. Typical examples of particles are liposomes and bacterial cells or parts thereof, such as membranes. Whole cells are generally killed or their reproduction is hindered in order to avoid problems associated with infection.

In all cases, the actual structure of the carrier is unimportant since it is the size of the carrier which acts to increase the immunogenic response. When soluble macromolecules, such as proteins and polysaccharides, are used as carriers, molecular weights in the range of 10,000 to 1,000,000 are preferred. If sufficiently large, the protein or polysaccharide carrier may be insoluble and thus be considered to be a particulate material.

The method of attaching a peptide to the carrier is unimportant so long as the immunogenic spcificity of the peptide is retained at least in part. A preferred method of achieving this result is to attach a peptide to the carrier by means of an amide bond formed between a carboxylic acid or amino group of the carrier and an amino or carboxylic acid group of the peptide, particularly a free carboxylic acid or amino terminal group of the peptide. Another preferred method of bonding is the formation of an ester bond between a carboxylic acid or hydroxy group of the carrier and a hydroxy or carboxylic acid group of the peptide, preferably a terminal carboxylic acid group of the peptide. Linking groups, e.g. terminal diamines with 1 to 10 methylene carbons joining the amines, can be used if desired.

When a carrier is used, the immunogenic response can be enhanced by bonding multiple peptides to the surface of the carrier. For example, from 1 to 100,000 peptides can be bound to a protein or polysaccharide with 100 to 10,000 being preferred. When proteins are used as a carrier, amphoteric proteins are preferred. Such proteins have a liphophilic portion and a hydrophilic portion. In such proteins, it is preferred to attach peptides of the invention to the hydrophilic region, thereby exposing them to the humoral environment when the lipophilic region becomes embedded in various membranes.

One preferred protein for use as a carrier is the LTB protein, the name being derived from "labile toxin, part B", a material previously suggested for use as an immunogenic carrier.

The preferred embodiments listed above for use with macromolecule carriers also apply for use with particulate carriers except that the upper limit of peptides per carrier is approximately $10^{15}$, preferably $10^{10}$. Bacterial cells (killed or otherwise made non-infective or hindered from reproducing) are the preferred particulate materials.

The advent of the recombinant DNA technology has lead to a recent and rapid increase in the number of techniques available for producing cloned gene products. Examples of recent U.S. patents which describe methods suitable for producing cloned genes suitable for use in the present invention include U.S. Pat. Nos. 4,419,450, 4,418,194, 4,414,150, 4,399,216, 4,394,443, 4,356,270, 4,351,901, and 4,237,224. Of course, it is also possible to modify the techniques described therein by synthesizing DNA sequences capable of expressing the desired peptide product and inserting them into suitable cloning vectors as described in U.S. Pat. Nos. 4,273,875, 4,304,863, 4,332,901, 4,403,036, 4,363,877, and 4,349,629. The following description sets forth genetic engineering procedures in general which are suitable for use with this invention.

Genetic information is encoded on double-stranded deoxyribonucleic acid ("DNA" or "genes") according to the order in which the DNA coding strand presents the characteristic bases of its repeating nucleotide components. "Expression" of the encoded information to form polypeptides involves a two-part process. According to the dictates of certain control regions ("regulons") in the gene, RNA polymerase may be caused to move along the coding strand, forming messenger RNA (ribonucleic acid) in a process called "transcription." In a subsequent "translation" step the cell's ribosomes in conjuction with transfer RNA convert the mRNA "message" into a peptide or polypeptide. Included in the information mRNA transcribed from DNA are signals for the start and termination of ribosomal translation, as well as the identity and sequence of the amino acids which make up the peptide or polypeptide. The DNA coding strand comprises long sequences of nucleotide triplets called "codons" because the characteristic bases of the nucleotides in each triplet or codon encode specific bits of information. For example, 3 nucleotides read at ATG (adenine-thymine-guanine) result in an mRNA signal interpreted as "start translation", while termination codons TAG, TAA and TGA are interpreted "stop translation". Between the start and stop codons lie the so-called structural gene, whose codons define the amino acid sequence ultimately translated. That definition proceeds according to the well-established "genetic code" (e.g., J. D. Watson, Molecular Biology of the Gene, W. A. Benjamin Inc., N.Y., 3rd ed. 1976) which describes the codons for the various amino acids. The genetic code is degenerate in the sense that different codons may yield the same amino acid, but precise in that for each amino acid there are specific codons and none other. Thus, for example, all of the codons TTT, TTC, TTA and TTG, when read as such, encode for serine and no other amino acid. During translation the proper reading phase or reading frame must be maintained. Consider for example what happens when the ribosome reads different bases as the beginning of a codon (underlined) in the sequence

... GCTGGTTGTAAG ... ;

... <u>GCT</u> <u>GGT</u> <u>TGT</u> <u>AAG</u> ... ⟶

... Ala—Gly—Cys—Lys ...

G <u>CTG</u> <u>GTT</u> <u>GTA</u> AG ... ⟶ ... Leu—Val—Leu ...

... GC <u>TGG</u> <u>TTG</u> <u>TAA</u> A ... ⟶ ... Trp—Leu—(STOP).

The polypeptide ultimately produced, then, depends vitally upon the spatial relationship of the structural gene with respect to the regulon.

A clearer understanding of the process of genetic expression will emerge once certain components of genes are defined:

Operon—A gene comprising structural gene(s) for polypeptide expression and the control region ("regulon") which regulates that expression.

Promoter—A gene within the regulation to which RNA polymerase must bind for initiation of transcription.

Operator—A gene to which repressor protein may bind, thus preventing RNA polymerase binding on the adjacent promoter.

Inducer—A substance which deactivates repressor protein, freeing the operator and permitting RNA polymerase to bond the promoter and commence transcription.

Catabolite Activator Protein ("CAP") Binding Site—A gene which binds cyclic adenosine monophosphate ("cAMP")mediated CAP, also commonly required for initiation of transcription. The CAP binding site may in particular cases be unnecessary. For example, a promoter mutation in the lactose operon of the phage plac UV5 eliminates the requirement for cAMP and CAP expression. J. Beckwith et al, J. Mol. Biol. 69, 155-160 (1972).

Promoter-Operator System—An operable control region of an operon, with or without respect to its inclusion of a CAP binding site or capacity to code for repressor protein expression.

Further by way of definintion, and for use in the discussion of recombinant DNA which follows, we define the following:

Cloning Vehicle—Non-chromosomal double stranded DNA comprising an intact "replicon" such that the vehicle is replicated, when placed within a unicellular organism ("microbe") by a process of "transformation". An organism so transformed is called a "transformant".

Plasmid—For present purposes, a cloning vehicle derived from viruses or bacteria, the latter being "bacterial plasmids".

Complementarity—A property conferred by the base sequences of single strand DNA which permits the formation of double stranded DNA through hydrogen bonding between complementary bases on the respective strands. Adenine (A) complements thymine (T), while guanine (G) complements cytosine (C).

Advances in biochemistry in recent years have led to the construction of "recombinant" cloning vehicles in which, for example, plasmids are made to certain exogenous DNA. In particular instances the recombinant may include "heterologous" DNA, by which is meant DNA that codes for polypeptides ordinarily not produced by the organism susceptible to transformation by the recombinant vehicle. Thus, plasmids are cleaved to provide linear DNA having ligatable termini. These are bound to an exogenous gene having ligatable termini to provide a biologically functional moiety with an intact replicon and a desired phenotypical property. The recombinant moiety is inserted into a microorganism by transformation and transformants are isolated and cloned, with the object of obtaining large populations capable of expressing the new genetic information. Methods and means of forming recombinant cloning vehicles and transforming organisms with them have been widely reported in the literature. See, e.g., H. L. Heynecker et al, Nature 263, 748-752 (1976); Cohen et al, Proc. Nat. Acad. Sci. USA 69, 2110 (1972); ibid., 70, 1293 (1973); ibid., 70, 3240 (1973); ibid., 71, 1030 (1974); Morrow et al, Proc. Nat. Acad. Sci. USA 71, 1743 (1974) and Jackson et al, ibid, 69, 2904 (1972). A generalized discussion of the subject appears in S. Cohen, Scientific American 233, 24 (1975). These and other mentioned publications are incorporated herein by reference.

A variety of techniques are available for DNA recombination, according to which adjoining ends of separate DNA fragments are tailored in one way or another to facilitate ligation. The latter term refers to the formation of phosphodiester bonds between adjoining nucleotides, most often through the agency of the enzyme T4 DNA ligase. Thus, blunt ends may be directly ligated. Alternatively, fragments containing complementary single strands at their adjoining ends are advantaged by hydrogen bonding which positions the respective ends for subsequent ligation. Such single strands, referred to as cohesive termini, may be formed by the addition of nucleotides to blunt ends using terminal transferase, and sometimes simply by chewing back one strand of a blunt end with an enzyme such λ-exonuclease. Again, and most commonly, resort may be had to restriction endonucleases, which cleave phosphodiester bonds in and around unique sequences of nucleotides of about 4–6 base pairs in length. Many restriction endonucleases and their recognition sites are known,, the so-called Eco RI endonuclease being most widely employed. Restriction endonucleases which cleave double-stranded DNA at rotationally symmetric "palindromes" leave cohesive termini. Thus, a plasmid or other cloning vehicle may be cleaved, leaving termini each comprising half the restriction endonuclease recognition site. A cleavage product of exogenous DNA will have ends complementary to those of the plasmid termini. Alternatively, as disclosed infra, synthetic DNA comprising cohesive termini pending insertion of exogenous DNA, the termini can be digested with alkaline phosphatase, providing molecular selection for clones incorporating the exogenous fragment. Incorporation of a fragment having the proper orientation relative to other aspects of the vehicle may be enhanced when the fragment supplants vehicle DNA excised by two different restriction endonucleases, and itself comprises termini respectively constituting half the recognition sequence of the different endonucleases.

A recombinant cloning vehicle containing one of these DNA sequences is also included within the scope of the present invention. This cloning vehicle may be a microbial or yeast plasmid or a bacteriophage and the like. One particularly preferred cloning vehicle is λgt11. A unicellular organism containing a DNA sequence as discussed above which is capable of expressing an immunologically active peptide capable of inducing in a human an immune response which is cross reacted with and protective against a malarial parasite is accordingly included within the scope of the present invention when the DNA sequence has been artificially introduced into the unicellular organism. *E. Coli* are preferred hosts.

The invention also includes a method for inducing immunization against malaria which comprises administering an immunologically effective amount of a peptide of the invention to a human. The appropriate therapeutically effective dose can be determined readily by those skilled in the art and will usually be in the range of about 0.01 μg/kg to about 100 μg/kg of body weight. More preferably, the dosage is in the range of about 0.1 to about 1.0 μg/kg.

The mode of administration of peptides of the invention may be by any suitable route which delivers the peptide to the host. For the purposes of the present invention, the peptide may be administered intramuscularly, interveneously, or by any other method which enables the active ingredient to reach lymphocytes and induce an immune response.

Peptides of the invention may be prepared as pharmaceutical compositions containing immunogenic amount of the peptide as an active ingredient in a nontoxic and sterile pharmaceutically acceptable carrier. Aqueous suspensions or solutions containing the active material in a form ready for injection are preferred. Conventional adjuvants can, of course, be used to enhance the immune response if desired.

It is preferred that the peptides of the invention, when in a pharmaceutical preparation, be present in unit dosage forms. When intended for human use, these amounts can easily be calculated from the dosage rates previously given by assuming an average body weight of 70 kg. Accordingly, a preferred unit-dose-containing pharmaceutical prepration would contain from about 7 to about 70 μg of active ingredient. It will be understood, however, that the specific dose level for any particular patient will depend upon a variety of factors including the activity of the specific compound employed; the age, general health, sex, and diet of the patient; the time of administration; the route of administration; the rate of excretion; possible synergistic effects with any other drugs being administered; and the degree of protection being sought. Of course, the administration can be repeated at suitable intervals if necessary.

This application uses the standard nomenclature and abbreviations of biochemistry for peptide and DNA sequences. An example publication setting forth the standard nomenclature used in this application for peptide and DNA sequences is Lehninger, *Biochemistry*, Worth publishers, New York, 1970, particularly chapters 4 and 5 (peptides) and 12 (DNA).

The invention having been generally described, the same will be better understood by reference to certain specific examples which are included herein for purpose of illustration only and are not intended to be limiting of the invention or any embodiment thereof, unless specified.

EXAMPLE

Clones from the Genomic DNA Expression Library

The *P. vivax* genomic DNA library in the expression vector was produced as follows. The expression library was made from the DNA of an uncloned parasite supplied by the Center for Disease Control, Atlanta, Ga.

Parasitized blood was routinely collected in heparin sulfate (20 U ml$^{-1}$ blood) when the parasitemia was 4 to 6% as judged by giemsa-stained blood smears. Adenosine diphosphate (ADP) was added (0.5 mg ml$^{-1}$) and the infected blood passed sequentially over one column of acid washed glass beads equilibrated with phosphate-buffered saline (PBS) and two columns of CF-11 cellulose equilibrated with PBS to remove platelets and leukocytes, respectively. All column volumes were equal to the starting blood volume. Red cells were collected by centrifugation for 10 min at 1500 rpm at 20° C. The majority of parasites were freed from intact red blood cells by lysis in one packed red cell volume of 0.15% (w/v) saponin in k-1 buffer (*Dame et al., Science* 225:593, 1984) and centrifuged at 2500 rpm for 10 min. The pellet was washed once in 4 packed red cell volumes of K-1 buffer and used immediately or frozen in solid CO$_2$/ethanol and stored at −40° C.

Extraction of DNA. DNA was extracted from fresh or frozen pellets of saponin treated parasites by resuspending the cells at room temperature in 10–20 pellet volumes of 50 mM Tris-HCl/50 mM EDTA/100 mM NaCl, pH 8.0, followed by an equal volume of the same buffer containing 1% sodium dodecyl sulphate (SDA). Proteinase K was added (approx. 0.1 mg ml$^{-1}$) and the mixture incubated at 37° C. for 2 h. Ethidium bromide was added (0.6 mg ml$^{-1}$), and the preparation mixed with 1.35 volumes of a saturated solution of CsCl in the above buffer and centrifuged for 18 h at 45000 rpm in a Beckman VTi50 rotor at 20° C. The DNA band was removed by puncturing the side of the tube with a syringe fitted with a 16 gauge needle. Ethidium bromide was removed from the DNA by repeated isopropanol extraction. CsCl was removed by dialysis against 10 mM Tris-HCl/1 mM EDTA, pH 8.0, and the DNA was extracted once with a mixture of buffer saturated phenol/ choloroform/isoamyl alohol (25:24:1, v/v/v) and once with chloroform/isoamyl alcohol (24:1, v/v). The DNA was spooled from the solution onto a glass rod after the addition of 0.1 volume of 3 M sodium acetate, pH 6.5, and 3 volumes of ice cold ethanol. This DNA preparation is contaminated with host DNA, but the level of contamination is less than 50% as judged by hybridization and it does not complicate the present results.

P. vivax DNA thus obtained was digested in the presence of DraI restriction endonuclease, and fragments, about 800-1300 base pairs in length, were isolated after agarose gel electrophoresis. Fragments were ligated into cleaved pasmid pUC9. Recombinant plasmids were transfected into the E. coli strain, JM83. Colonies were treated as described by Thayer, Anal. Biochem. 98:60-63 (1979).

Overnight broth cultures of colonies isolated after transfection were spotted on nitrocellulose filters (Schleicher and Schuell No. BA85-82 mm disks) which had been placed on L-Broth-1% agar petri plates containing 100 μg/ml diaminopimelic acid, 10 μg/ml thymidine, and 25 μg/ml ampicillin (ampicillin being the selective marker originally used in screening the transfectants). The cultures were transferred to the filter using a replicate plating device capable of transferring 42 samples, each with a volume of 2μl, from a microtiter dish containing 0.2-ml aliquots of the overnight cultures. The filters were then incubated at 37° C. for 48 to 60 h, allowing the colonies to reach a diameter of 3 to 4 mm.

After growth the colonies were lysed and the DNA fixed to the filter by a series of five steps. Initially, the cells were treated with lysozyme to convert the cells to spheroplasts, making them more susceptible to detergent lysis. This was done by placing the nitrocellulose filter for 1 min on a stack of Whatman No. 1 filter disks saturated with 1.5 mg/ml lysozyme (Worthington No. L500-02932) in 25% sucrose-50 mM Tris HCl, pH 8.0. The filter was then removed and blotted for 1 min on a strip of dry Whatman 3MM paper. The absorption and blotting procedure was repeated two more times. To complete cell lysis and denature the DNA, the nitrocellulose filter was placed on a stack of filter disks saturated with 0.2% Triton X-100-0.5 N NaOH. The same triple absorption and blotting procedure was used with this and all subsequent steps. The filters were always treated and blotted with the surface of the filter bearing colonies kept upright to prevent spreading of the colonies or loss of DNA. To insure complete denaturation of the DNA the filter was then treated with 0.5 N NaOH alone. To neutralize the sodium hydroxide, the filter was treated with 1 M Tris HCl, pH 7.5. Finally, the filter was equilibrated with 0.15 M NaCl-0.1 M Tris HCl, pH 7.5. All treatments were carried out at room temperature (23°-30° C.) except the lysozyme treatment which was done at 40° C. The filter was then air-dried and baked in vacuo for 2 h at 80° C. The top filter in the Whatman 3MM stacks may be removed before treatment of a new nitrocellulose filter is initiated, but this is not essential.

Colonies containing the circumsporozoite protein gene were detected with radiolabeled oligonucleotide. The following four oligonucleotide probes from region II common to P. knowlesi and P. falciparum (4) were used:

CCATG$_C{}^T$AGTGTAAC$_C{}^T$TGTGGAAATGGT.

The filters were hybridized with the probe at 42° C. for 18 hours in 4X Denhardt's (0.08 percent polyvinyl pyrolidone, 0.08 percent ficoll and 0.08 percent bovine serum albumin, BSA), 2X SSC, and 0.1 percent SDS. The filters were washed with 0.5X SSC and 0.2 percent SDS at 37° C. A positive colony (pPvl) was detected by autoradiography.

Monoclonal antiboides (MAb) used for these experiments (219c and 427) were derived from Balb/c mice immunized with sporozoites of the ONG strain of P. vivax from Vietnam and react with P. vivax sporozoites from North Korea, Thiland and Colombia. MAb 219c gave a circumsporozoite precipitin test with P. vivax sporozoites and identified proteins of 46 to 57 kDa in an immunoblot assay using SDS solubilized P. vivax sporozoites.

Tests indicating the correctness of the peptide sequence were performed as follows. Immulon II plates (Dynatech) were coated with purified MAb 219c. Serial 10-fold dilutions of synthetic peptide from 100 μg/ml to 10 ng/ml were incubated with the MAbs. After overnight incubation the plates were washed and incubated with horseradish peroxidase labeled MAb 219c for 2 hours. Substrate was then added to determine the amount of enzyme-linked antibody bound. There was a strongly positive reaction down to 100 ng/ml of peptide with anti- P. vivax MAb 219c. As a control for specificity, an anti- P. falciparum sporozoite MAb was coated on the plate. No P. vivax synthetic peptide bound to the anti-P. falciparum MAb. This indicated that antibodies directed towards the circumsporozoite gene of P. vivax were inhibited from binding sporozoites of P. vivax by competition with the synthetic peptide. Therefore, it was concluded that the synthetic peptide resembled the immunodominate region of the circumsporozoite protein.

It is understood that the examples and embodiments described herein are for illustrative purposes only and that various modifications or changes in light thereof will be suggested to persons skilled in the art and are to be included within the spirit and purview of this application and the scope of the appended claims.

We claim:

1. A synthetic peptide having an amino acid sequence: Gly-Asp-Arg-Ala-Asp-Gly-Gln-Pro-Ala.

2. The peptide of claim 1 capable of inducing antibodies protective against malarial infection caused by Plasmodium vivax sporozoites when said peptide is administered in immunogenic amount in a pharmaceutically acceptable carrier to a host.

3. The peptide of claim 2 being conjugated with an adjuvant.

4. The peptide of claim 2 wherein said carrier is nontoxic bacterial cell or a liposome.

* * * * *